US009579353B2

(12) United States Patent
Olmstead

(10) Patent No.: US 9,579,353 B2
(45) Date of Patent: *Feb. 28, 2017

(54) PHARMACEUTICAL COMPOSITIONS CONTAINING PEDIOCOCCUS AND METHODS FOR REDUCING THE SYMPTOMS OF GASTROENTEROLOGICAL SYNDROMES

(75) Inventor: Stephen F. Olmstead, Reno, NV (US)

(73) Assignee: PROTHERA, Inc., Reno, NV (US)

(*) Notice: Subject to any disclaimer, the term of this patent is extended or adjusted under 35 U.S.C. 154(b) by 319 days.

This patent is subject to a terminal disclaimer.

(21) Appl. No.: 13/067,582

(22) Filed: Jun. 10, 2011

(65) Prior Publication Data
US 2012/0315249 A1  Dec. 13, 2012

(51) Int. Cl.
A23L 1/29 (2006.01)
A23L 1/308 (2006.01)
A61K 31/00 (2006.01)
A61K 31/70 (2006.01)
A61K 38/47 (2006.01)
A61K 35/744 (2015.01)
A61K 45/06 (2006.01)
A61K 35/747 (2015.01)
A61K 47/00 (2006.01)

(52) U.S. Cl.
CPC .......... A61K 35/744 (2013.01); A23L 33/135 (2016.08); A23L 33/21 (2016.08); A61K 35/747 (2013.01); A61K 45/06 (2013.01); A23Y 2280/00 (2013.01)

(58) Field of Classification Search
None
See application file for complete search history.

(56) References Cited

U.S. PATENT DOCUMENTS 8,021,656 B2 * 9/2011 Corthesy-Theulaz ............. A61K 35/745
424/93.45
2006/0008511 A1 * 1/2006 Lin et al. ................. 424/442
2011/0091431 A1 * 4/2011 Olmstead ............... 424/93.44

OTHER PUBLICATIONS

Cleale et al., 1990. Effect of Inoculation of Whole Plant Corn Forage with Pediococcus acidilactici and Lactobacillus xylosus on Preservation of Silage and Heifer Growth. Journal of Dairy Science, vol. 73, Issue 3, pp. 711-718).*
De Man et al. 1960. A Medium for the Cultivation of Lactobacilli. Journal of Applied Bacteriology, vol. 23, No. I, pp. 130-135.*
Biswas et al. 1991. Influence of Growth Conditions on the Production of a Bacteriocin, Pediocin AcH, by Pediococcus acidilactici H. Applied and Environmental Microbiology, vol. 57, No. 4, April, pp. 1265-1267.*
Herstad et al. 2010. Effects of a probiotic intervention in acute canine gastroenteritis—a controlled clinical trial. Journal of Small Animal Practice, vol. 51, No. I, January, On Line Publication, Dec. 2009, pp. 34-38.*
Krigsman. A. 2007. Gastrointestinal Pathology in Autism: Description and Treatment. Medical Veritas, vol. 4, pp. 1522-1530.*
Lenard. 2009. LE Magazine, Jan. 2009, 8 Pages.*
Matthews . 2010. Autism Diets and Nutrition Providing Health benefits to Many Children with ASD. Autism Advocate, Second Edition 2010, pp. 54-58.*

* cited by examiner

Primary Examiner — Debbie K Ware
Assistant Examiner — Kailash C Srivastava
(74) Attorney, Agent, or Firm — Isaac Angres

(57) ABSTRACT

The invention provides a method and composition for ameliorating or reducing the symptoms, signs, and markers and for the treatment of irritable bowel syndrome, inflammatory bowel disease or gastritis in a mammal in need thereof, said method comprising administering effective amounts of a pharmaceutically acceptable composition containing at least one probiotic microorganism strain comprising *Pediococcus* for a time sufficient to ameliorate, reduce or treat at least one symptom, sign, or marker of irritable bowel syndrome, inflammatory bowel disease or gastritis.

21 Claims, No Drawings

PHARMACEUTICAL COMPOSITIONS CONTAINING PEDIOCOCCUS AND METHODS FOR REDUCING THE SYMPTOMS OF GASTROENTEROLOGICAL SYNDROMES

FIELD OF INVENTION

The present invention relates, in general, to novel probiotic microorganisms and their therapeutic uses. More particularly, it relates, as well as their tolerance of gastric acid and bile salts. Also, this invention relates to a prophylactic and therapeutic composition comprising the same for contributing in many probiotic ways to the host's general health and preventing and treating diseases or conditions associated with gastroinstestinal diseases.

BACKGROUND OF THE INVENTION

Disorders involving abnormal functioning of the gastrointestinal tractafflict large segments the world's population. The most prevalent of the functional disorder in the absence of structural abnormalities is irritable bowel syndrome (IBS). The most common inflammatory gastrointestinal diseases are inflammatory bowel disease (IBD, which includes Crohn's disease, ulcerative colitis and indeterminate colitis) and gastritis. These conditions profoundly affect the quality of life of sufferers, and incur significant economic costs (Engel & Neurath, 2010; Loftus et al., 2000; Longstreth et al., 2006; Madden & Hunter; Salonen et al., 2010). IBS is estimated to affect 5 million Americans. IBS is characterized by recurring symptoms of abdominal pain, bloating, and altered bowel function in the absence of structural abnormalities. IBD affects between 2 to 6 percent of Americans. IBD is characterized by frequent and progressive symptoms of abdominal pain, diarrhea, rectal bleeding, and weight loss. Gastritis is estimated to affect 4.5 million people in the United States. Gastritis involves a chronic inflammation of the stomach, leading to upper abdominal pain and nausea. Gastritis is also the main cause of acquired failure of the gastric acid barrier, which results in the development of duodenal and gastric ulcers and stomach cancer in patients with *H. pylori* infection.

There is now evidence that these complex disorders have something in common: an imbalance (dysbiosis) between protective and harmful gastrointestinal organisms, even when no specific pathogen can be identified (Blaser, 1998; Bullock et al., 2004; Collins et al., 2009; Corthesy et al., 2007; Lin, 2004; Ott et al., 2004; Pimental et al., 2011; Salonen, et al., 2010). The role of dysbiosis in these diseases provides the rationale for the use of agents such as antibiotics, which alter the microbial composition of the GI tract. However, the use of antibiotics has been linked to serious side effects, complications, and bacterial resistance (Engel & Neurath, 2010; Grundmann et al., 2010). Moreover, antimicrobial therapies provide inferior results compared with antimicrobial therapies for other common infectious diseases (Camilleri & Tack, 2010; Rimbara et al., 2011).

IBS is classified as a functional disorder because there is no sign of disease when the small intestine and colon are examined. IBS is characterized by recurring symptoms of abdominal pain, bloating, and altered bowel function in the absence of structural abnormalities (see Brandt et al., 2009; Chang & Talley, 2010; Grundman et al., 2010). According to the Rome II criteria, IBS sufferers can be grouped into three symptom subtypes based on the stool form, stool frequency and defecatory symptoms: diarrhea predominant (IBS-D), constipation predominant (IBS-C), and mixed subtype (IBS-M) with alternating episodes of both diarrhea and constipation. More recently, the Rome III criteria, which focus on the stool form over the defecation frequency, have been issued (Longstreth et al., 2006). The most important physiological aberrations in IBS include visceral hypersensitivity, abnormal gut motility and autonomous nervous system dysfunction, the interactions of which are suggested to make the bowel function susceptible to a number of exogenous and endogenous factors, such as the GI microbiota, diet and psychosocial factors.

The presence of low-level inflammation in the GI mucosa of IBS patients has also been observed. Several studies have examined the fecal flora of IBS patients and found a decrease in *Escherichia coli*, lactobacilli, and bifidobacteria and an increase in aerobic microorganisms in comparison with healthy volunteers (Jonkers & Stockbrugger, 2007; Madden & Hunter, 2002; Salonen et al., 2010).

Inflammatory bowel disease (IBD) is a chronic inflammatory condition that includes Crohn's disease and ulcerative colitis (Longstreth et al., 2006; Engel & Neurath, 2010; Loftus et al., 2000). The causes of IBD are not known, but a leading theory suggests that some agent, perhaps a virus or bacterium, alters the body's immune response, triggering an inflammatory reaction in the intestinal wall. Crohn's disease most commonly affects the small intestine and/or the colon, whereas ulcerative colitis affects the large intestine, primarily the sigmoid/rectal region of the large bowel. The diagnosis of IBD is suggested by the symptoms of abdominal pain, rectal bleeding, and diarrhea. The ultimate diagnosis relies on a combination of history, endoscopic finding, histologic features, and negative stool studies for infectious agents (Silverberg et al., 2005). Cases that cannot be diagnosed as either ulcerative colitis or Crohn's disease are called indeterminate colitis. No specific microorganism has yet been described as a possible causal factor in IBD. However, a change in the bacterial composition of both the fecal and mucosal microbiota has been observed (Ott et al., 2004).

Gastritis involves a chronic inflammation of the stomach and duodenum that is typically associated with *H. pylori* infection. Upper abdominal pain and nausea are the most common symptoms; other symptoms are indigestion, abdominal bloating, nausea, and vomiting. Gastritis may be associated with pernicious anemia. The main acute causes of gastritis are excessive alcohol consumption or prolonged use of nonsteroidal anti-inflammatory drugs (also known as NSAIDs) such as aspirin or ibuprofen. Gastritis may develop after major surgery, traumatic injury, burns, severe infections, weight loss surgery involving the banding or reconstruction of the digestive tract, chronic bile reflux, stress, and certain autoimmune disorders. Gastroscopy, a blood test, urea breath test, and/or stool test may be used to diagnose gastritis (Sepulveda & Patil, 2010).

The standard treatment for gastritis has been a one week "triple therapy" consisting of proton pump inhibitors and the antibiotics clarithromycin and amoxicillin, but the emergence of drug resistance has compromised the use of this regimen (Camilleri & Tack, 2010; Rimbara et al., 2011). The antibiotics ciprofloxacin and metronidazole have been used to treat gastritis, but the side effects of these antibiotics limits their use (Engel & Neurath, 2010; Grundman et al., 2010). A newer antibiotic, rifaximin, may be more effective than previous drugs (Pimental et al., 2010), but it is currently approved only for the treatment of traveler's diarrhea. IBD is usually treated with immunosuppressive agents. Frequently surgery is required. Therapy of IBS is directly at relieving symptoms and is often unsuccessful.

Because of studies suggesting that dysbiosis is important in the etiology of these disorders, there has been interest in identifying probiotic compositions that are capable of ameliorating the symptoms of IBS, IBD, and gastritis and improving the response to conventional treatments.

Additionally, it is well known that probiotics are described as "live microorganisms, which, when administered in adequate amounts, confer a health benefit on the host" (reports of the United Nations Food and Agricultural Organization and the World Health Organization, Alternative Medicine 2001). Probiotics are widely applied as nutritional supplements in animals and humans. For example, yeast is used as a nutrient supplement for livestock, and yogurt with lactic acid bacteria *Lactobacillus* and/or *Bifidobacterium* is commonly used to prevent and treat diarrhea-related gastrointestinal (GI) infectious diseases. Multiple unique properties of probiotics such as anti-infectious properties, immune modulatory effects, enhanced barrier functions, metabolic effects and alternations of intestinal mobility or function make probiotics an effective type alternative medicine for animals and humans.

Although probiotic products such as short-chain fatty acids (SCFA), cell wall peptidoglycan and short chain DNA fragments containing CpG sequences can have beneficial probiotics effects, the administration of live microorganisms to animals and humans remains the core application and focus of research studies of probiotics. In order to have the maximum effects of probiotics on animals and humans, one has to administrate live bacteria to reach gastrointestinal tracts for multiplication. *Lactobacillus* spp and *Bifidobacterium* spp are two most commonly probiotic genera described in scientific literature and in commercial products. Both *Lactobacillus* spp and *Bifidobacterium* spp are facultative or strict anaerobic bacteria. Most species (or strains) of *Lactobacillus* and *Bifidobacterium* are sensitive to the exposure of oxygen and high temperature. It is difficult to maintain the viability of *Lactobacillus* and *Bifidobacterium* at room temperature under consistent open and closure operations. Therefore, variable results are often described, especially for commercially available products that are required to have long term storage and shipping in various temperature.

In sum, there is a high frequency of incomplete or absent response of IBS, IBD and gastritis to current medical therapies. Thus there has gone unmet a need for improved methods, compositions, etc. that can ameliorate one or more symptoms associated with these diseases. Effective dietary and/or pharmaceutical interventions for these conditions could have a major public health impact. The present systems and methods, etc., provide these and/or other advantages.

OBJECTS OF THE INVENTION

Accordingly, it is an object of the present invention to provide probitoic compositions for treating gastroenterological medical conditions.

Another object of the present invention is to provide methods for treating gastroenterological conditions using probitoic therapy.

It is a further object of the instant invention to treat irritable bowel syndrome with probiotics such as *Pediococcuc*.

These and other objects of the present invention will more readily become apparent from the description and examples which follow.

SUMMARY OF THE INVENTION

The instant invention provides a method for ameliorating the symptoms, reducing the symptoms and the treatment of irritable bowel syndrome, inflammatory bowel disease or gastritis in a mammal in need thereof, said method comprising administering effective amounts of a pharmaceutically acceptable composition containing at least one strain of *Pediococcus* for a time sufficient to ameliorate, reduce or treat at least one symptom of irritable bowel syndrome, inflammatory bowel disease or gastritis.

The invention also provides a pharmaceutically acceptable composition comprising at least one strain of *Pediococcus* in an amount sufficient to ameliorate at least one symptom of irritable bowel syndrome, inflammatory bowel disease, or gastritis in a mammal in need thereof.

DESCRIPTION OF THE PREFERRED EMBODIMENTS

Diagnosis and Pathophysiology

In one aspect the compositions, methods, systems, etc., herein are directed to providing probiotic compositions that are capable of reducing one or more signs or symptoms of IBS, IBD, and gastritis in individuals in need thereof.

The signs and symptoms of gastritis, which can be reduced by the methods, compositions, etc. of the present invention, include: a gnawing or burning ache or pain (indigestion) in the upper abdomen that may become either worse or better with eating; nausea; vomiting; loss of appetite; belching or bloating; a feeling of fullness in the upper abdomen after eating; weight loss; gastric ulcer; duodenal ulcer; inflammation of the stomach lining; a positive test for urease in the stool; a positive urea breath test.

The signs and symptoms of IBS, which can be reduced by the methods, compositions, etc. of the present invention include: abdominal pain or cramping; a bloated feeling; gas (flatulence); diarrhea or constipation; a change in frequency of bowel movements; a change in appearance of bowel movements; feelings of uncontrollable urgency to have a bowel movement; and mucus in the stool.

The signs and symptoms of IBD (Crohn's disease, ulcerative colitis and indeterminate colitis) that can be reduced by the methods, compositions, etc. of the present invention include: abdominal pain; fever; loss of appetite; pain with passing stool; diarrhea; unintentional weight loss; constipation; rectal bleeding; bloody stools; intestinal inflammation, abscesses and fistulas; and inflammation of the ileal pouch (pouchitis).

It is not necessary that individuals have been diagnosed with a microbial infection in order to benefit from the compositions, methods, systems, etc., herein.

The compositions, formulations, methods, etc., can be used as dietary supplements or as food additives or as pharmaceutical agents or otherwise as desired to reduce symptoms of IBS, IBD and gastritis. The methods herein include methods, kits, labels, systems, etc., directed to labeling, marketing and otherwise providing the compositions to health care professionals and/or to consumers for use in reducing symptoms of IBS, IBD and gastritis.

The inclusion of at least one strain of *Pediococcus* in the composition is essential for this invention.

In one embodiment, the composition is comprised of a mixture of a first microbial organism comprising at least one strain of *Pediococcus* and at least one second microbial organism having a beneficial health effect in humans, wherein the second microbial organism is at least one of a bacterium or fungus. Typically, at least one additional microbial organism is selected from the group comprising *Lactobacillus*, *Bifidobacterium*, *Streptococcus*, or *Saccharomyces*.

In a further embodiment, the compositions are provided in capsules or other suitable administration formats, and a single capsule provides a full serving. In one example, each capsule comprises at least about 1 million and up to 150 billion Colony Forming Units (CFU) of the *Pediococcus* per 1 capsule serving and at least about 1 million CFU of the additional microorganism per 1 capsule serving. In another embodiment, the yield is about 150 billion CFU per gram of material. Other yields can also be used as desired.

In a further embodiment, the *Pediococcus* strain is one or more of *Pediococcus acidilactici*, *Pediococcus pentosaceus*, *Pediococcus damnosus*, *Pediococcus dextrinicus*, *Pediococcus cerevisiae*, or *Pediococcus parvulus*.

In one preferred embodiment, *Pediococcus acidilactici* is used.

In another embodiment, the selected species of *Pediococcus* is combined with one or more further probiotics. The additional probiotic may be any microorganism that has a beneficial health effect in humans. Typically, the additional probiotic is one or more of: *Lactobacillus acidophilus*, *L. brevis*, *L. bulgaricus*, *L. casei*, *L. crispatus*, *L. curvatus*, *L. fermentum*, *L. gasseri*, *L. helveticus*, *L. johnsonii*, *L. paracasei*, *L. paraplantarum*, *L. pentosus*, *L. plantarum*, *L. reuteri*, *L. rhamnosus*, *L. salivarius*, *L. sakei*, *Lactococcus lactis*, *Leuconostoc lactis*, *Ln. pseudomesenteroides*, *Ln. mesenteroides*, *Bifidobacterium adolescentis*, *B. animalis*, *B. bifidum*, *B. breve*, *B. lactis*, *B. longum*, *B. infantis*, *Streptococcus thermophilus*, *Saccharomyces boulardii*, *Saccharomyces cereviseae*, *Bacillus subtilis*, *B. coagulans* (frequently mislabeled as *Lactobacillus* sporogenes), *B. lichenifonnis*, *B. cereus*, *Enterococcus faecium*, *Escherichia coli* Nessle 1917, *Proprionibacterium acidipropionici*, *P. freudenreichii*, *P. jensenii*, and *P. thoenii*.

In a further embodiment, none of the probiotic organisms in the composition have been or are propagated or grown in media containing casein or gluten.

In another further embodiment, the composition such as a dietary supplement is a dried powder, a tablet, or a gelatin capsule. Exemplary methods for encapsulation of probiotics can be found, e.g., in U.S. Patent Appl. 2007/0122397 and in the scientific literature.

In one further embodiment, the composition is supplied along with an ingestible support material for human consumption. Exemplary ingestible support materials include a cereal based product, rice cake, soy cake, food bar product, cold formed food bar product, custard, pudding, gelatin, rice milk, soy milk, yogurt, kefir, mashed fruit product, candy, candy bar, and applesauce. Numerous methods for formulation of ingestible support materials with probiotics are known in the literature.

In another embodiment the product can be a kit or system wherein the compositions, capsules, etc., herein are contained in a pharmaceutically acceptable container and a written description, brochure, information sheet, catalog, or label explaining the product can reduce one or more symptoms of IBS, IBD or gastritis or the product is free of casein and gluten and/or hypoallergenic. Further, the product can be marketed together with the written description, brochure, information sheet, catalog, or label explaining the product can reduce one or more symptoms of IBS, IBD or gastritis/gastric ulcer, and/or the product is free of casein and gluten. In an additional embodiment the product is marketed together with a written description, brochure, information sheet, catalog, or label explaining that the product is hypoallergenic.

Probiotic Ingredients and Compositions

"Probiotics" within the context of the present invention is used in accord with its usual meaning, for example as selected, viable microbial dietary supplements that, when introduced in sufficient quantities, beneficially affect the human organism via their effects in the gastrointestinal tract (Holzapfel et al., 2001; Holzapfel & Schillinger, 2002). The FAO/WHO has adopted the definition of probiotics as "Live microorganisms which when administered in adequate amounts confer a health benefit on the host" (FAO/WHO guidelines, 2002). These beneficial bacteria may be found for example in milk or in milk processing factories, living or decaying plants, and also in the intestines of man and animals.

Currently, the best-studied probiotics are the lactic acid bacteria, particularly *Lactobacillus* spp. and *Bifidobacterium* spp. *Lactobacillus* is a genus of Gram-positive facultative anaerobic bacteria. The genus *Lactobacillus* currently comprises over 100 species and encompasses a wide variety of organisms. They are common and usually benign. In humans they are present in the vagina and the gastrointestinal tract, where they are symbiotic and make up a small portion of the gut flora (Tannock, 1999). Studies in humans have been done with *L. acidophilus*, *L. salivarius*, *L. johnsonii*, *L. casei*, *L. lactis*, *L. reuteri*, *L. plantarum*, *L. rhamnosus*, *L. brevis*, *L. gasseri*, and other species and subspecies. The use of *Lactobacillus* species in human studies has been extensively reviewed in the scientific literature, including the references provided herein.

*Bifidobacterium* is a genus of Gram-positive anaerobic bacteria, currently comprised of 31 characterized species, 11 of which have been detected in human feces (Tannock, 1999). Bifidobacteria are Gram-positive, irregular or branched rod-shaped bacteria that are commonly found in the intestines of humans and most animals and insects. While *B. infantis*, *B. brevi*, and *B. longum* are the largest group of bacteria in the intestine of infants, Bifidobacteria are said to be only the 3rd or 4th largest group in adults (and comprise only 3-6% of adult fecal flora). Bifidobacteria inhibit the growth of *Candida albicans*, *E. coli*, and other pathogenic bacteria *B. infantis* has been shown to dramatically reduce the symptoms of irritable bowel syndrome (IBS) (Whorwell et al., 2006).

Lactobacilli and *Bifidobacteria* have been examined for their effectiveness in the prevention and treatment of a diverse spectrum of gastrointestinal disorders. Among other benefits, these organisms are thought to restore and maintain immune system function and gastrointestinal barrier function, and to reduce inflammation (Corthesy et al., 2007; Parvez et al., 2006).

The effects of *Lactobacillus* and *Bifidobacterium* in humans have been reviewed by Jonkers & Stockbruegger, 2007; Lesbros-Pantoflickova; Moayyedi et al., 2010; Gareau et al., 2010; Parvez et al., 2006; Lesbros-Pantoflickova D, et al. 2007). Midolo et al. (1995) reported that six strains of *L. acidophilus* and one strain of *L. casei* subsp. *rhamnosus* inhibited the growth of *H. pylori* growth in vitro. The administration of *Lactobacillus* and Bifidobacteria improves gastritis; the effect is statistically significant but weak (Lesbros-Pantoflickova D, et al. 2007). One product, known as VSL#3, has been shown to reduce the symptoms of ulcerative colitis and pouchitis (inflammation of the ileal pouch; reviewed by Corthesy et al., 2007). A probiotic/prebiotic mixture known as Synbiotic 2000 had no effect on the postoperative recurrence of Crohn's disease (Chemesh, 2007).

*Saccharomyces boulardii* is a transient yeast probiotic long used to treat various types of diarrhea. It is a hardy, acid-resistant, temperature tolerant microorganism that is not affected by antibiotics. *S. boulardii* has been reported to have beneficial effects in patients with Crohn's disease, IBS, and gastritis (Guslandi et al., 2000; Choi et al., 2011; Szajewska et al., 2010).

*Pediococcus* can be described as "the only acidophilic, homofermentative, lactic acid bacteria that divide alternatively in two perpendicular directions to form tetrads" (Simpson and Taguchi, 1995). Phylogenetically, *Pediococcus* and *Lactobacillus* form a super-cluster that can be divided in to two sub-clusters. All species of *Pediococcus* fall within the *Lactobacillus casei—Pediococcus* sub-cluster. Morphologically, pediococci (cocci; 0.6-1.0 mm in diameter) and lactobacilli (rods) are distinct. Five species currently belong to the genus *Pediococcus: Pediococcus acidilactici, Pediococcus damnosus, Pediococcus dextrinicus, Pediococcus parvulus,* and *Pediococcus pentosaceus.*

*P. pentosaceus* is used as an acid producing starter culture in sausage fermentations, cucumber and green bean fermentations, soya milk fermentations, and silage, and is a typical component of the microflora of most cheese varieties during ripening. *Pediococcus* species have been used as probiotics in the livestock and pet industries (US Patent Appl. 20060008511 and 20070020328) and are generally recognized as safe for human consumption (GRAS) (Ishibashi & Yamazaki, 2001). One strain of *P. acidilactici* (LMG P-21927) has been isolated from human feces (Speelmans et al; US Patent Appl. 2006/0165661; WO2004/110466). The antimicrobial effects of *Pediococcus* on foodborne pathogens such as *Listeria* have been determined. The antibacterial properties of *Pediococcus* are due to bactericidal peptides known as pediocins, which are of great interest as food biopreservatives. Several studies have been done to examine the effects of pediocins on *H. pylori*. Kim et al. (2003) reported that purified pediocin PO2 had weak activity against *H. pylori*, but Midolo and coworkers (1995) found no effect of live *Pediococcus* on *H. pylori*. None of the studies contemplate the use of live *Pediococcus* for the treatment of gastritis, IBS or IBD in humans.

We previously disclosed compositions and methods comprising *Pediococcus* for use in humans (U.S. published application No. 2011/0091431 whose contents are incorporated by reference herein). The present invention specifies the use of these compositions and methods for reducing the signs and/or symptoms of gastritis, IBS and IBD in persons in need thereof.

Although not necessary to an understanding of the compositions, methods, etc., herein the beneficial effects of our compositions in reducing symptoms of IBS, IBD and gastritis may result from an effect of *Pediococcus* as an immune modulator, which reduces inflammation and enhances the host response against disease. The dosage of *Pediococcus* is also important for successful colonization of the gastrointestinal tract. Without being bound by theory, these properties may allow the *Pediococcus* compositions herein to confer or restore a more normal neurogastrointestinal and immunological function in individuals with IBS, IBD and gastritis. Therefore, individuals that have been diagnosed with IBS, IBD or gastritis may benefit from the new compositions.

The compositions discussed herein may be administered, for example, as dietary supplements, food and beverage additives, food and beverage ingredients, and pharmaceutical agents. Any suitable administration route can be used, typically alimentary/orally.

The compositions discussed herein can include or be used in combination with compositions comprising digestive enzymes. For example, the compositions can be used in combination with a formulated combination of digestive enzymes known as ENZYMAID™ (Kirkman Labs, Oregon) and a wide variety of other formulations. Typically, the digestive enzymes will be administered as a separate tablet or capsule or powder. A digestive enzyme formulation may if desired be given to a patient for a proscribed period of time prior to the initiation of treatment, for example for a period of 1-3 days to 1-4 weeks prior to initiation of treatment with the compositions described herein. Examples of digestive enzyme formulations that are suitable for use in the present invention include, but are not limited to, the products from ProThera Inc. and Klaire Labs, Inc. (Reno, Nev.), known as VITALZYMES™ COMPLETE; VITALZYMES™ FORTE; VITALZYMES™ CHEWABLES; and SERENAID®, and any of the ingredients therein.

The compositions described herein may be used subsequent to treatment with antibiotic or antifungal agents, or concomitantly with such treatments.

The compositions discussed herein may be used in conjunction with a gluten-free and casein-free diet. Thus, the methods and compositions of the present invention can be used in conjunction with any of the methods and compositions in Houston (U.S. Pat. No. 6,447,772) and/or Wilkinson (U.S. Pat. No. 6,251,391) including the SERENAID® brand enzyme product from ProThera, Inc.

The compositions herein are preferably comprised of the following ingredients (% by relative CFU content):
*Pediococcus acidilactici* 1% to 99%
*Pediococcus pentosaceus* 1% to 99%
*Pediococcus damnosus* 1% to 99%
*Pediococcus dextrinicus* 1% to 99%
*Pediococcus parvulus* 1% to 99%
*Bifidobacterium lactis* 1% to 99%
*Bifidobacterium animalis* 0% to 99%
*Bifidobacterium adolescentis* 0% to 98%
*Bifidobacterium bifidum* 0% to 98%
*Bifidobacterium breve* 0% to 98%
*Bifidobacterium infantis* 0% to 98%
*Bifidobacterium longum* 0% to 98%
*Lactobacillus acidophilus* 0% to 98%
*Lactobacillus brevis* 0% to 98%
*Lactobacillus bulgaricus* 0% to 98%
*Lactobacillus casei* 0% to 98%
*Lactobacillus crispatus* 0% to 98%
*Lactobacillus curvatus* 0% to 98%
*Lactobacillus fermentum* 0% to 98%
*Lactobacillus gasseri* 0% to 98%
*Lactobacillus helveticus* 0% to 98%
*Lactobacillus johnsonii* 0% to 98%
*Lactobacillus paracasei* 0% to 98%
*Lactobacillus paraplantarum* 0% to 98%
*Lactobacillus pentosus* 0% to 98%
*Lactobacillus plantarum* 0% to 98%
*Lactobacillus reuteri* 0% to 98%
*Lactobacillus rhamnosus* 0% to 98%
*Lactobacillus sakei* 0% to 98%
*Lactobacillus salivarius* 0% to 98%
*Lactococcus lactis* 0% to 98%
*Leuconostoc lactis* 0% to 98%

*Leuconostoc pseudomesenteroides* 0% to 98%
*Leuconostoc mesenteroides* 0% to 98%
*Saccharomyces boulardii* 0% to 98%
*Saccharomyces cereviseae* 0% to 98%
*Streptococcus thermophilus* 0% to 98%
*Bacillus subtilis* 0% to 98%
*Bacillus coagulans* 0% to 98%
*Bacillus licheniformis* 0% to 98%
*Bacillus cereus* 0% to 98%
*Enterococcus faecium* 0% to 98%
*Escherichia coli* Nessle 1917 0% to 98%
*Proprionibacterium acidipropionic* 0% to 98%
*Proprionibacterium freudenreichii* 0% to 98%
*Proprionibacterium jensenii* 0% to 98%
*Proprionibacterium thoenii* 0% to 98%
*Enterococcus faecium* 0% to 98%

The above ingredients can also be present, for example, at ranges of more than 10%, 20%, 30%, 40%, 50%, 60%, 70%, 80%, 90%, or less than 90%, 80%, 70%, 60%, 50%, 40%, 30%, 20%, 10%.

In one embodiment, the compositions contain the following amounts of ingredients per 1 capsule serving size, where CFU means a Colony Forming Unit:
*Pediococcus acidilactici* 1.5 billion CFU (6.0%)
*Bifidobacterium breve* 0.5 billion CFU (2.0%)
*Bifidobacterium infantis* 0.5 billion CFU (2.0%)
*Lactobacillus paracasei* 0.5 billion CFU (2.0%)
*Lactobacillus salivarius* 0.5 billion CFU (2.0%)
*Bifidobacterium lactis* 1.0 billion CFU (4.0%)
*Bifidobacterium longum* 1.0 billion CFU (4.0%)
*Streptococcus thermophilus* 1.0 billion CFU (4.0%)
*Lactobacillus bulgaricus* 1.0 billion CFU (4.0%)
*Lactobacillus casei* 2.5 billion CFU (10.0%)
*Lactobacillus plantarum* 2.5 billion CFU (10.0%)
*Lactobacillus acidophilus* 3.0 billion CFU (12.0%)
*Bifidobacterium bifidum* 3.5 billion CFU (14.0%)
*Lactobacillus rhamnosus* 6.0 billion CFU (24.0%)

It will be understood that a variety of different mixtures of *Lactobacillus, Bifidobacterium, Sachharomyces, Lactococcus,* and other probiotic organisms can be combined with *Pediococcus* in various % compositions and doses that produce efficacious results; the invention is not limited to the exact formulation described above.

Methods for formulation and encapsulation of bacteria have been reported, and such methods may be used in conjunction with this invention (e.g. US Patent Appl. 2004/247580).

In addition, the compositions, methods, etc., herein can be formulated, made or used to include prebiotic agents that promote the growth of probiotic organisms in the gastrointestinal tract. Suitable prebiotic agents include, but are not limited to, fructooligosaccharides, galactooligosaccharides, lactulose, β-glucan, inulin, pectin and resistant starch (see, e.g., Paul et al., U.S. Pat. No. 6,241,983).

The probiotic compositions of the invention are also formulated with other therapeutic agents such proton pump inhibitors selected from the group consisting of Omeprazole, lansoprazole, rabeprazole, pantoprazole and esomeprazole and 112-receptor antagonists selected from the group consisting of Cimetidine, Ranitidine, Famotidine and Nizatidine.

EXAMPLE 1

A 38 year-old male patient with severe abdominal distention is treated daily with a capsule containing 200 million CFU of *Pedioccocus acidilactici*. The patient is evaluated on a weekly basis and the patient reports improvement of the symptoms of abdominal distention.

EXAMPLE 2

An 8 year-old boy with daily gas, abdominal craps, and constipation is treated by administering 2 capsules twice daily, each capsule containing a probiotic formulation containing *Pediococcus acidilactici* 1.5 billion colony forming units (CFU), *Bifidobacterium breve* 0.5 billion CFU, *Bifidobacterium infantis* 0.5 billion CFU, *Lactobacillus paracasei* 0.5 billion CFU, *Lactobacillus salivarius* 0.5 billion CFU, *Bifidobacterium* lactis 1.0 billion CFU, *Bifidobacterium longum* 1.0 billion CFU, *Streptococcus thermophilus* 1.0 billion CFU, *Lactobacillus bulgaricus* 1.0 billion CFU, *Lactobacillus casei* 2.5 billion CFU, *Lactobacillus plantarum* 2.5 billion CFU, *Lactobacillus acidophilus* 3.0 billion CFU, *Bifidobacterium bifidum* 3.5 billion CFU, and *Lactobacillus rhamnosus* 6.0 billion CFU and experiences complete resolution of symptoms after 3 weeks.

The entire contents including the references cited therein of the references cited above and the following patents, published applications including all their foreign equivalents and journal publications are incorporated by reference in their entirety for all purposes to the same extent as if each individual patent, patent application or publication were so individually denoted.

| US Patent Documents | | |
| --- | --- | --- |
| US Patent | Date | Inventor |
| 5,705,152 | January, 1998 | Plummer |
| 5,501,857 | March, 1996 | Zimmer |
| 6,080,401 | June, 2000 | Reddy, et al. |
| 6,241,983 | June, 2001 | Paul et al. |
| 6,251,391 | June, 2001 | Wilkinson, et al. |
| 7,241,441 | July, 2007 | Choi, et al. |

| US Patent Applications | | |
| --- | --- | --- |
| US Patent Application | Publication Date | Inventor |
| 2004/0247580 | Dec. 9, 2004 | Chung et al. |
| 2006/0165661 | Jul. 27, 2006 | Speelmans, et al. |
| 2007/0286916 | Dec. 13, 2007 | Bengmark |
| 2010/0196323 | Aug. 5, 2010 | Plail, et al. |
| 2009/0263366 | Oct. 22, 2009 | Lin |
| 2005/0186188 | Aug. 25, 2005 | Guo |
| 2006/0251633 | Nov. 9, 2006 | Salvadori, et al. |
| 2006/0008511 | Jan. 12, 2006 | Lin & Lin |
| 2007/0020328 | Jan. 25, 2007 | Lin |
| 2010/0278975 | Nov. 4, 2010 | Chung, et al. |
| Docket No. 1776-004-02 | Oct. 9, 2009 | Olmstead |

| World Patent Documents | | |
| --- | --- | --- |
| WO2004/103083 | Dec. 2, 2004 | Ljungh-Wadstrom |
| WO2004/110466 | Dec. 23, 2004 | Speelmans G, et al. |
| WO2010/002054. | Jan. 7, 2010 | Chung Myung Jun et al. |

OTHER REFERENCES

1. Brandt L J, Chey W D, Foxx-Orenstein A E, et al. An evidence-based position statement on the management of irritable bowel syndrome. Am J Gastroenterol 2009; 104 Suppl 1:S1-S35.

2. Blaser M J. Helicobacters are indigenous to the human stomach: duodenal ulceration is due to changes in gastric microecology in the modern era. Gut 1998; 43:721-727

3. Bullock N R, Booth J C, Gibson G R. Comparative composition of bacteria in the human intestinal microflora during remission and active ulcerative colitis. Curr Issues Intest Microbiol 2004; 5(2): 59-64.

4. Camilleri M, Tack J F. Current medical treatments of dyspepsia and irritable bowel syndrome. Gastroenterol Clin North Am 2010; 39(3):481-93.

5. Chang J Y and Talley N J. Current and emerging therapies in irritable bowel syndrome: from pathophysiology to treatment. Trends Pharmacol Sci 2010; 31(7):326-34.

6. Chemesh I, et al. Failure of Synbiotic 2000 to prevent postoperative recurrence of Crohn's disease. Dig Dis Sci 2007; 52:385-389.

7. Choi C H, et al. A randomized, Double-blind, placebo-controlled multicenter trial of *Saccharomyces boulardii* in irritable bowel syndrome: effect on quality of life. J Clin Gastroenterol 2011 Feb. 4. [Epub ahead of print]

8. Collins S M, et al. The putative role of the intestinal microbiota in the irritable bowel syndrome. Dig Liver Dis 2009; 41(12):850-3.

9. Corthesy B, Gaskins H R, Mercenier A. Cross-talk between probiotic bacteria and the host immune system. J Nutr 2007; 137:781 S-790S.

10. Engel M A, Neurath M F. New pathophysiological insights and modern treatment of IBD. J Gastroenterol 2010; 45(6):571-83.

11. FAO/WHO (2002). Guidelines for the evaluation of probiotics in food. London, Ontario, Canada, April 30 and May 1, 2002.

12. Gareau M G, Sherman P M, Walker W A. Probiotics and the gut microbiota in intestinal health and disease. Nat Rev GastroenterolHepatol 2010; 7:503-514.

13. Grundmann O, Yoon S L, Moshiree B. Current developments for the diagnosis and treatment of irritable bowel syndrome. Curr Pharm Des. 2010; 16(33):3668-45.

14. Guslandi M, et al. *Saccharomyces boulardii* in maintenance treatment of Crohn's disease. Dig Dis Sci 2000; 45:1462-4.

15. Holzapfel W H, Schillinger U. Introduction to pre and probiotics. Food Res Int 2002; 35:109-116.

16. Holzapfel W H, et al. Taxonomy and important features of probiotic microorganisms in food and nutrition. Am J Clin Nutr 2001; 73(2 Suppl):365S-73S.

17. Ishibashi N, Yamazaki S. Probiotics and safety. Am J Clin Nutr 2001; 73(2 Suppl):465S-470S.

18. Jonkers D, Stockbriigger R. Review article: Probiotics in gastrointestinal and liver diseases. Aliment Pharmacol Ther 2007; 26 (Supplement s2):133-148.

19. Kang J S, Lee M S. Anti-*Helicobacter pylori* activity of *Pediococcus acidilactici* GMB7330 isolated from infant feces. Korean J Microbiol 2005; 41(2):152-156.

20. Kim T-S, et al. Antagonism of *Helicobacter pylori* by bacteriocins of lactic acid bacteria. J Food Prot 2003; 66(1):3-12.

21. Kruszewska K, et al. Selection of lactic acid bacteria as probiotic strains by in vitro tests. Microecol Ther 2002; 29:37-51.

22. Lesbros-Pantoflickova D, Corthesy-Theulaz I, Blum A L. *Helicobacter pylori* and probiotics. J Nutr 2007; 137(3 Suppl 2):812S-8S.

23. Lin, H C. Small intestinal bacterial overgrowth—a framework for understanding irritable bowel syndrome. JAMA 2004; 292:852-858.

24. Loftus E V, Silverstein Md., Sandborn W J, et al. Ulcerative colitis in Olmsted County, Minnesota, 1940-1993: incidence, prevalence, and survival. Gut 2000; 46:336-343.

25. Longstreth G F, et al. Functional bowel disorders. Gastroenterology 2006; 130:1480-149.

26. Madden J A J, Hunter J O. A review of the role of the gut microflora in irritable bowel syndrome and the effects of probiotics. Br J Nutr 2002; 88 Suppl 1:S67-S72

27. Midolo P D, et al. In vitro inhibition of *Helicobacter pylori* NCTC 11637 by organic acids and lactic acid bacteria. J Appl Bacteriol 1995; 79(4):475-9.

28. Moayyedi P, et al. The efficacy of probiotics in the treatment of irritable bowel syndrome: a systematic review. Gut 2010; 59(3):325-32.

29. Ott S J, et al. Reduction in diversity of the colonic mucosa associated bacterial microflora in patients with active inflammatory bowel disease Gut 2004; 53:685-693.

30. Parvez S, Malik K A, Ah Kang S, Kim H Y. Probiotics and their fermented food products are beneficial for health. J Appl Microbiol 2006; 100:1171-85.

31. Pimentel M, Lembo T, Chey W D, et al. Rifaximin therapy for patients with irritable bowel syndrome without constipation. N Engl J Med 2011; 364:22-32.

32. Rimbara E, Fischbach L A, Graham D Y. Optimal therapy for *Helicobacter pylori* infections. Nat Rev Gastroenterol Hepatol. 2011; 8(2):79-88.

33. Salonen A, de Vos W M, and Palva A. Gastrointestinal microbiota in irritable bowel syndrome: present state and perspectives. Microbiology 2010; 156:3205-3215.

34. Sepulveda A R, Patil M. Practical approach to the pathologic diagnosis of gastritis. Arch Pathol Lab Med. 2008; 132(10):1586-93.

35. Silverberg M S, et al. Toward an integrated clinical, molecular and serological classification of inflammatory bowel disease. Report of a working party of the 2005 Montreal World Congress of Gastroenterology. Can J Gastroenterol 2005; 19 Suppl A:5A-36A.

36. Simpson W J, Taguchi H. The genus *Pediococcus*, with notes on the genera *Tetratogenococcus* and *Aerococcus*, In Wood B J B, Holzapfel W H (eds). The Genera of Lactic Acid Bacteria. 1995; pp. 125-172; Chapman & Hall, London.

37. Szajewska H, Horvath A, Piwowarczyk A. Meta-analysis: the effects of *Saccharomyces boulardii* supplementation on *Helicobacter pylori* eradication rates and side effects during treatment. Aliment Pharmacol Ther 2010; 32(9):1069-79.

38. Tannock G W. Identification of lactobacilli and bifidobacteria. Current Issues Molec Biol 1999; 1:53-64.

39. Whorwell P J, Altringer L, Morel J, et al. Efficacy of an encapsulated probiotic *Bifidobacterium infantis* 35624 in women with irritable bowel syndrome. Am J Gastroenterol 2006; 101:1581-90.

Although the present invention has been described with reference to specific details of certain embodiments thereof, it is not intended that such detail should be regarded as limitations upon the scope of the invention, except as and to the extent that they are included in the accompanying claims.

What is being claimed is:

1. A method for ameliorating or reducing the symptoms and for the treatment of irritable bowel syndrome; and ulcerative colitis in a mammal in need thereof, said method comprising administering an effective amount of a pharmaceutically acceptable composition containing within a carrier material suitable for human consumption the following formulation of Colony Forming Units (CFU) of probiotic microorganisms:

Pediococcus acidilactici 1.5 billion CFU
Bifidobacterium breve 0.5 billion CFU
Bifidobacterium infantis 0.5 billion CFU
Lactobacillus paracasei 0.5 billion CFU
Lactobacillus salivarius 0.5 billion CFU
Bifidobacterium lactis 1.0 billion CFU
Bifidobacterium longum 1.0 billion CFU
Streptococcus thermophiles 1.0 billion CFU
Lactobacillus bulgaricus 1.0 billion CFU
Lactobacillus casei 2.5 billion CFU
Lactobacillus plantarum 2.5 billion CFU
Lactobacillus acidophilus 3.0 billion CFU
Bifidobacterium bifiidum 3.5 billion CFU and
Lactobacillus rhamnosus 6.0 billion CFU, for a time sufficient to ameliorate, reduce or treat at least one symptom, sign, or marker of irritable bowel syndrome and ulcerative colitis.

2. The method according to claim 1, wherein the symptom that is ameliorated is selected from the group consisting of: a gnawing or burning ache or pain in the upper abdomen; nausea; vomiting; loss of appetite; belching or bloating; a feeling of fullness in the upper abdomen after eating; weight loss; gastric ulcer; duodenal ulcer; inflammation of the stomach lining; a positive test for urease in the stool; a positive test for urea in the breath; gas; flatulence; diarrhea or constipation; a change in frequency of bowel movements; a change in appearance of bowel movements; feelings of uncontrollable urgency to have a bowel movement; mucus in the stool; pain with passing stool; rectal bleeding; bloody stools; intestinal inflammation; intestinal abscesses and/or fistulas; and pouchitis.

3. The method according to claim 1 or 2, wherein said composition further comprising Pediococcus selected from the group consisting of: Pediococcus pentosaceus, Pediococcus damnosus, Pediococcus dextrinicus, Pediococcus parvulus and mixtures thereof.

4. The method according to claim 3, wherein the Pediococcus is present in an amount that comprises from about 1 million to about 150 billion CFU.

5. The method according to claim 4, wherein the amount comprises about 150 billion CFU of the Pediococcus per gram of said pharmaceutically acceptable composition.

6. The method according to claim 1, wherein said composition further comprises Saccharomyces.

7. The method according to claim 1, further comprising Lactobacillus brevis, Lactobacillus crispatus, Lactobacillus curvatus, Lactobacillus fermentum, Lactobacillus gasseri, Lactobacillus helveticus, Lactobacillus johnsonii, Lactobacillus paraplantarum, Lactobacillus pentosus, Lactobacillus reuteri, Lactobacillus sakei, Bifidobacterium adolescentis, Bifidobacterium animalis, Saccharomyces boulardii, and Saccharomyces cerevisiae and mixtures thereof.

8. The method according to claim 1, further comprising Lactococcus lactis, Leuconostoc lactis, Leuconostoc pseudomesenteroides, Leuconostoc mesenteroides, Bacillus subtilis, Bacillus coagulans, Bacillus licheniformis, Bacillus cereus, Enterococcus faecium, Escherichia coli Nessie 1917, Proprionibacterium acidipropionici, Propionibacterium freudenreichii, Propionibacterium jensenii, and Proprionibacterium thoenii.

9. The method according to claim 1, 6, 7 or 8, wherein none of the probiotic microorganisms in the composition have been propagated or grown in media containing casein.

10. The method according to claim 1, 6, 7 or 8, wherein none of the probiotic microorganisms in the composition have been propagated or grown in media containing gluten.

11. The method according to claim 1, 6, 7 or 8, wherein the pharmaceutically acceptable composition is labeled as a dietary supplement.

12. The method according to claim 11, wherein the pharmaceutically acceptable composition is formulated as a dried powder, a tablet, a hard gelatin capsule or a soft gelatin capsule.

13. The method according to claim 1, 6, 7 or 8, wherein the probiotic microorganisms are delivered orally in a single serving capsule.

14. The method according to claim 1, 6, 7 or 8, wherein the pharmaceutically acceptable composition is administered subsequent to administration of a digestive enzyme formulation.

15. The method of claim 1, wherein the carrier material is selected from the group comprising a cereal based product, rice cake, soy cake, food bar product, cold formed food bar product, custard, pudding, gelatin, rice milk, soy milk, yogurt, kefir, mashed fruit product, candy, candy bar, and applesauce.

16. The method according to claim 1, 6, 7 or 8, wherein the pharmaceutically acceptable composition is administered subsequent to administration of an antibiotic agent or antifungal agent.

17. The method according to claim 1, 6, 7 or 8, wherein the pharmaceutically acceptable composition is administered concomitantly with administration of an antibiotic agent or antifungal agent.

18. The method according to claim 17, wherein the antibiotic agent or antifungal agent is selected from the group consisting of: rifaximin, clarithromycin, azithromycin, amoxicillin, ampicillin, ciprofloxacin, metronidazole, vancomycin, nystatin, itraconazole, fluconazole, and a sulfonamide.

19. The method according to claim 1, wherein the pharmaceutically acceptable composition is administered in conjunction with a gluten-free and casein-free diet.

20. The method according to claim 1, wherein the pharmaceutically acceptable composition further comprises at least one prebiotic agent that promotes the growth of said probiotic microorganisms in the gastrointestinal tract.

21. The method according to claim 20, wherein the prebiotic agent comprises at least one of a fructooligosaccharide, galactooligosaccharide, lactulose, β-glucan, inulin, pectin and resistant starch.

* * * * *